United States Patent
Lu et al.

(10) Patent No.: US 10,640,465 B2
(45) Date of Patent: May 5, 2020

(54) METHOD FOR PREPARING PHENYLALANINE COMPOUND

(71) Applicant: SHENZHEN CHIPSCREEN BIOSCIENCES CO., LTD., Shenzhen, Guangdong (CN)

(72) Inventors: Xianping Lu, Guangdong (CN); Zhibin Li, Guangdong (CN); Xianghui Wang, Guangdong (CN)

(73) Assignee: SHENZHEN CHIPSCREEN BIOSCIENCES CO., LTD., Shenzhen, Guangdong (CN)

( * ) Notice: Subject to any disclaimer, the term of this patent is extended or adjusted under 35 U.S.C. 154(b) by 0 days.

(21) Appl. No.: 16/337,207

(22) PCT Filed: Sep. 27, 2017

(86) PCT No.: PCT/CN2017/103618
§ 371 (c)(1),
(2) Date: Mar. 27, 2019

(87) PCT Pub. No.: WO2018/059427
PCT Pub. Date: Apr. 5, 2018

(65) Prior Publication Data
US 2019/0225582 A1 Jul. 25, 2019

(30) Foreign Application Priority Data
Sep. 27, 2016 (CN) .......................... 2016 1 0855107

(51) Int. Cl.
*C07D 209/86* (2006.01)
*C07C 229/36* (2006.01)

(52) U.S. Cl.
CPC .......... *C07D 209/86* (2013.01); *C07C 229/36* (2013.01)

(58) Field of Classification Search
CPC .................................................... C07D 209/86
USPC ....................................................... 548/444
See application file for complete search history.

(56) References Cited

U.S. PATENT DOCUMENTS

| 7,268,157 B2 | 9/2007 | Lu et al. |
| 9,844,516 B2 | 12/2017 | Vela Hernandez et al. |
| 2012/0302568 A1 | 11/2012 | Vela Hernandez et al. |

FOREIGN PATENT DOCUMENTS

| CN | 1562970 A | 1/2005 |
| CN | 1882537 A | 12/2006 |
| CN | 104744282 A | 7/2015 |
| RU | 2569055 C2 | 11/2015 |
| WO | 2004048333 A1 | 6/2004 |

OTHER PUBLICATIONS

International Search Report for PCT/CN2017/103618 dated Jan. 4, 2018, ISA/CN.
Lan, Yukun, et al. Synthesis of chiglitazar, a new insulin sensitizer, Medicinal Chemistry, Chinese Journal of New Drugs, Aug. 30, 2004, vol. 13 No. 8, pp. 718-720.
First Office Action dated Jul. 18, 2019 for Russian patent application No. 2019112470, 8 pages.
Kumar,R. et al., Synthesis and evaluation of N-acetyl-L-tyrosine base d compounds as PPARα selective activators, European Journal of Medicina I Chemistry, 2007, vol. 42, No. 4, pp. 503-510.
Kumar,R. et al., Synthesis, in vitro and in silico evaluation of L-tyrosine containing PPARα/γ dual agonists, Bioorganic & Medicinal Chemistry, 2 0 0 7, vol. 15, No. 3, pp. 1547-1555.
First Office Action dated Jan. 28, 2020 for Japanese patent application No. 2019-517775, 5 pages, English translation provided by Global Dossier.

*Primary Examiner* — Kristin A Vajda
(74) *Attorney, Agent, or Firm* — Yue (Robert) Xu; Apex Attorneys at Law, LLP

(57) ABSTRACT

Disclosed is a method for preparing 2-(2-(4-fluorobenzoyl) phenylamino)-3-(4-(2-(9H-carbazol-9-yl)ethoxy)phenyl) propanoic acid. In the method 9-carbazole ethanol mesylate and methyl 2-[2-(4-fluorobenzoyl)phenyl)amino]-3-(4-hydroxyphenyl)propionate are used as starting materials, and subjected to condensation, hydrolysis and acidification to obtain the target compound. The preparation method of the present invention is suitable for industrial production, and the target compound has a high purity.

10 Claims, No Drawings

METHOD FOR PREPARING PHENYLALANINE COMPOUND

CROSS REFERENCE TO RELATED APPLICATIONS

The present disclosure is the national phase of International Application No. PCT/CN2017/103618, titled "METHOD FOR PREPARING PHENYLALANINE COMPOUND", filed on Sep. 27, 2017, which claims the priority to Chinese Patent Application No. 201610855107.3 titled "METHOD FOR PREPARING PHENYLALANINE COMPOUND", filed on Sep. 27, 2016 with the State Intellectual Property Office of the People's Republic of China, which is incorporated herein by reference in entirety.

FIELD

The present invention relates to the field of medicinal chemistry, specifically to a method for preparing a phenylalanine compound.

BACKGROUND 2-(2-(4-fluorobenzoyl)phenylamino)-3-(4-(2-(9H-carbazol-9-yl)ethoxy)phenyl)propanoic acid is a phenylalanine compound with therapeutic and preventive activity, which has the following chemical structural formula:

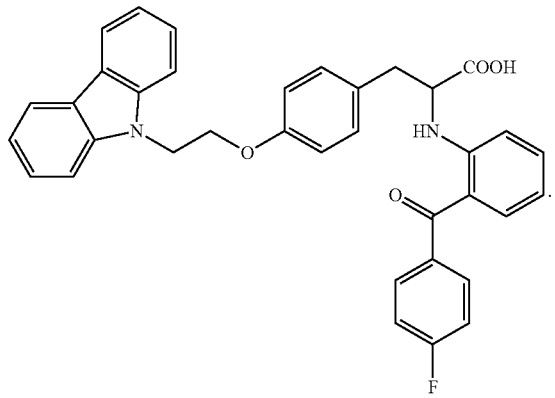 [SMILES: O=C(c1ccc(F)cc1)c1ccccc1NC(Cc1ccc(OCCn2c3ccccc3c3ccccc32)cc1)C(=O)O]

The pharmacological activity of the compound is described in Chinese patent application No. CN03126974.5 and U.S. Pat. No. 7,268,157. 2-(2-(4-fluorobenzoyl)phenylamino)-3-(4-(2-(9H-carbazol-9-yl)ethoxy)phenyl)propanoic acid is able to selectively activate PPAR-α, PPAR-γ and PPAR-δ, and can be used to treat the diseases associated with metabolic syndrome such as diabetes, hypertension, obesity, insulin resistance, hypertriglyceridemia, hyperglycemia, high cholesterol, arteries atherosclerosis, coronary heart disease, etc.

A preparation method of 2-(2-(4-fluorobenzoyl)phenylamino)-3-(4-(2-(9H-carbazol-9-yl)ethoxy)phenyl)propanoic acid is disclosed in Chinese patent application No. CN03126974.5 and U.S. Pat. No. 7,268,157, and the synthetic route thereof is as follows:

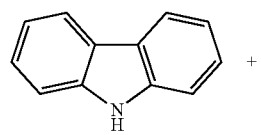

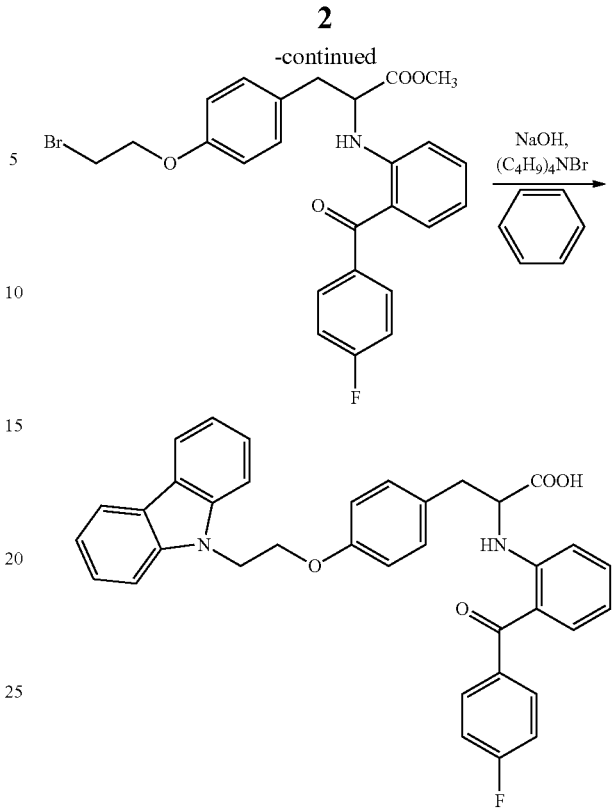

However, the method is accompanied by many side reactions, and the obtained product has many kinds of impurities and high impurity content, which are difficult to be removed by conventional treatment methods (including recrystallization). As a result, purification by chromatography is required, which makes it impossible to perform large-scale industrial production.

Therefore, discovery of the preparation methods of 2-(2-(4-fluorobenzoyl)phenylamino)-3-(4-(2-(9H-carbazol-9-yl)ethoxy)phenyl)propanoic acid suitable for industrial production is still of great importance.

SUMMARY

The object of the present disclosure is to overcome the disadvantages of the prior art and to provide an industrially acceptable process for the preparation of 2-(2-(4-fluorobenzoyl)phenylamino)-3-(4-(2-(9H-carbazol-9-yl)ethoxy)phenyl)propanoic acid.

The preparation method of 2-(2-(4-fluorobenzoyl)phenylamino)-3-(4-(2-(9H-carbazol-9-yl)ethoxy)phenyl)propanoic acid provided by the present disclosure is as follows:

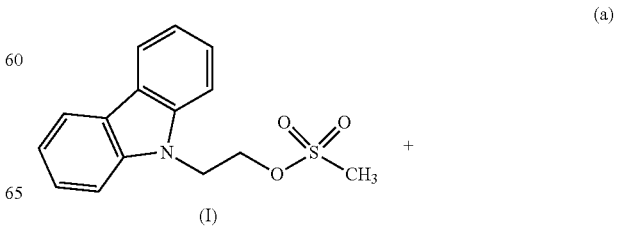

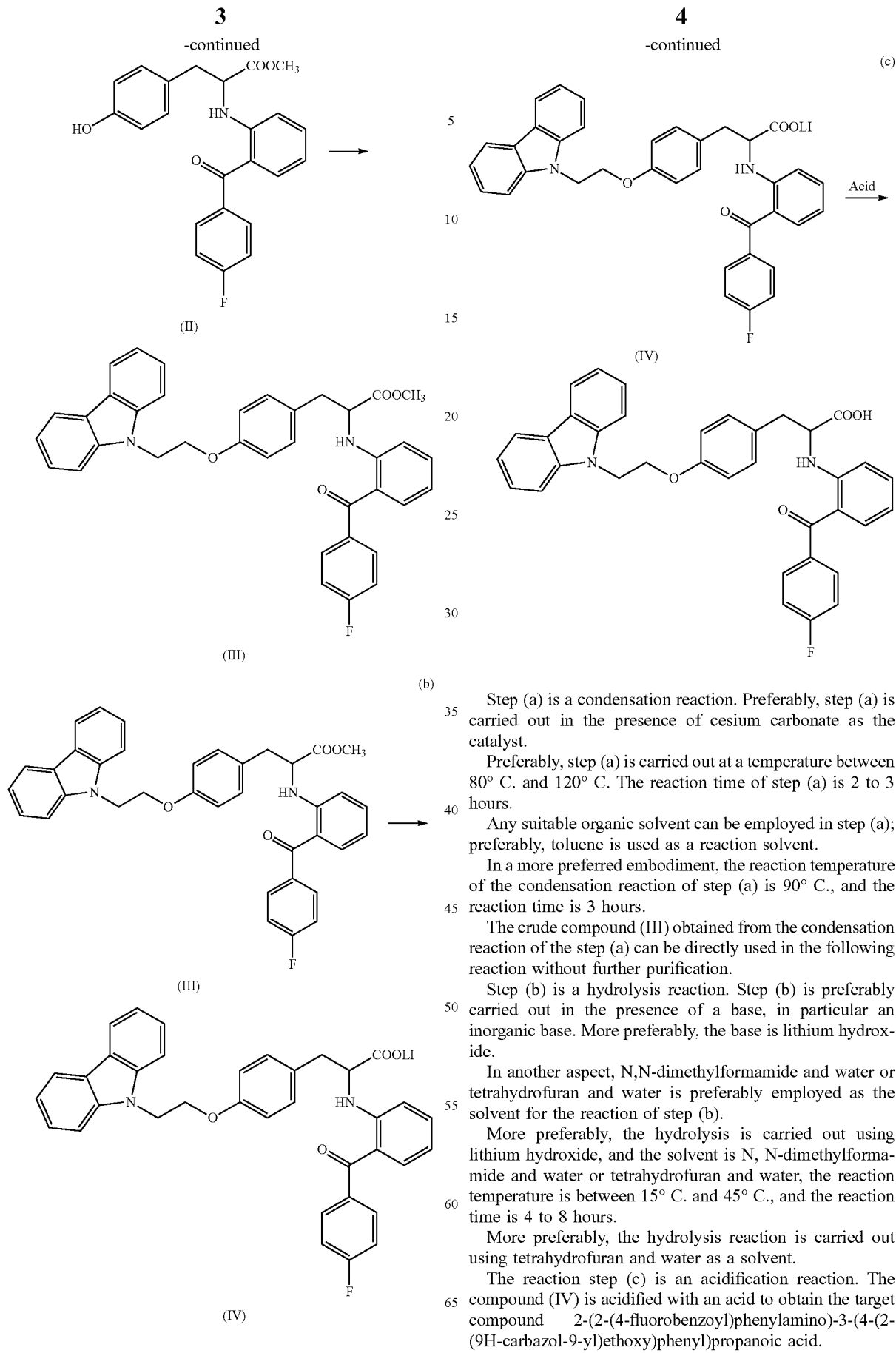

Step (a) is a condensation reaction. Preferably, step (a) is carried out in the presence of cesium carbonate as the catalyst.

Preferably, step (a) is carried out at a temperature between 80° C. and 120° C. The reaction time of step (a) is 2 to 3 hours.

Any suitable organic solvent can be employed in step (a); preferably, toluene is used as a reaction solvent.

In a more preferred embodiment, the reaction temperature of the condensation reaction of step (a) is 90° C., and the reaction time is 3 hours.

The crude compound (III) obtained from the condensation reaction of the step (a) can be directly used in the following reaction without further purification.

Step (b) is a hydrolysis reaction. Step (b) is preferably carried out in the presence of a base, in particular an inorganic base. More preferably, the base is lithium hydroxide.

In another aspect, N,N-dimethylformamide and water or tetrahydrofuran and water is preferably employed as the solvent for the reaction of step (b).

More preferably, the hydrolysis is carried out using lithium hydroxide, and the solvent is N, N-dimethylformamide and water or tetrahydrofuran and water, the reaction temperature is between 15° C. and 45° C., and the reaction time is 4 to 8 hours.

More preferably, the hydrolysis reaction is carried out using tetrahydrofuran and water as a solvent.

The reaction step (c) is an acidification reaction. The compound (IV) is acidified with an acid to obtain the target compound 2-(2-(4-fluorobenzoyl)phenylamino)-3-(4-(2-(9H-carbazol-9-yl)ethoxy)phenyl)propanoic acid.

Preferably, the acid used in the acidification reaction is an inorganic acid; more preferably, the acid is hydrochloric acid. The acidification reaction may be carried out using any suitable solvent, preferably ethyl acetate and water.

The product of the acidification reaction may optionally be recrystallized using an organic solvent.

Preferably, the organic solvent used for recrystallization is acetonitrile.

The above preferred conditions of the respective reaction steps of the present disclosure may be carried out in combination.

In another aspect, the present invention further provides use of compound (II) as the synthesis intermediate of 2-(2-(4-fluorobenzoyl)phenylamino)-3-(4-(2-(9H-carbazol-9-yl) ethoxy)phenyl)propanoic acid

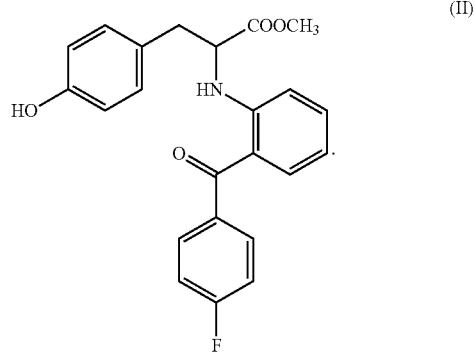 [SMILES: COC(=O)C(Cc1ccc(O)cc1)Nc1ccccc1C(=O)c1ccc(F)cc1]

(II)

The preparation method of the present disclosure does not require chromatographic separation and purification, and is suitable for industrial production; the obtained reaction product can be purified by simple recrystallization, and the obtained target compound has a high purity, which can be 99% or more.

DETAILED DESCRIPTION

The contents of the present disclosure are further described below with reference to examples, but the protection scope of the present disclosure is not limited to these examples. The percentages stated in the present disclosure are all percentages by weight unless otherwise specified. The range of values, such as units of measure or percentages, described in the specification are intended to provide an unambiguous written reference. Those skilled in the art will still be able to obtain the desired results based on the teachings and principles of the present disclosure, using temperatures, concentrations, amounts, etc. outside of this range or different from a single value.

Starting Materials and Experimental Instruments 9-carbazole ethanol mesylate: produced by Beijing Laviana Pharmtech Co., Ltd, purity >99%.

methyl 2-[2-(4-fluorobenzoyl)phenyl)amino]-3-(4-hydroxyphenyl)propionate, produced by Beijing Laviana Pharmtech Co., Ltd, purity >96%.

Proton nuclear magnetic resonance test conditions: instrument: AV-400 (Bruker, Germany); solvent: DMSO-$d_6$.

HPLC test conditions: instrument: Dionex UltiMate 3000; column: Shim-pack VP-ODS 5 µm 250 L×4.6; detector: VWD-3100.

LC-MS test conditions: instrument: Waters 2695/ZQ4000; column: Shim-pack VP-ODS 5 µm 150 L×2.0; detector: Waters 2996 DAD.

EXAMPLES

Example 1: Preparation of 2-(2-(4-fluorobenzoyl)phenylamino)-3-(4-(2-(9H-carbazol-9-yl)ethoxy)phenyl)propanoic Acid

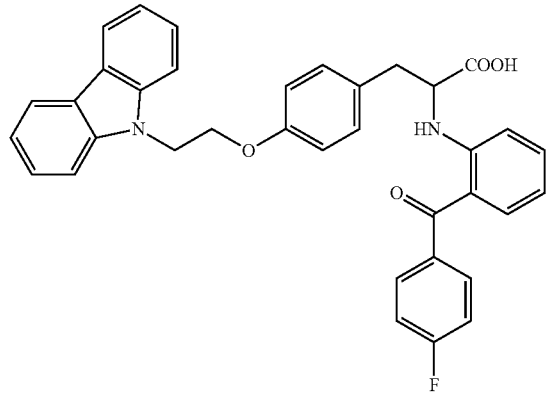 [SMILES: O=C(c1ccc(F)cc1)c1ccccc1NC(Cc1ccc(OCCn2c3ccccc3c3ccccc32)cc1)C(=O)O]

400 mL of toluene, 39.34 g (100 mmol) of methyl 2-[2-(4-fluorobenzoyl)phenyl)amino]-3-(4-hydroxyphenyl)propionate, 43.40 g (150 mmol) of 9-carbazole ethanol mesylate and 39.40 g (120 mmol) of cesium carbonate were sequentially added to a reaction flask, then the mixture was reacted at 90° C. for 3 hours before filtered, and the filtrate was concentrated in vacuo to remove the solvent toluene to give crude methyl 2-[2-(4-fluorobenzoyl)phenyl)amino]-3-(4-hydroxyphenyl)propionate. The purity (HPLC) was 69.8% and LC-MS (m/z) was 587 (M+1). The crude product obtained was used in the next step without further purification.

The above crude methyl 2-[2-(4-fluorobenzoyl)phenyl)amino]-3-(4-hydroxyphenyl) propionate and 400 mL of tetrahydrofuran were added to the reaction flask and dissolved with stirring at room temperature. 16.78 g (400 mmol) of LiOH.$H_2O$, which had been dissolved in 200 mL of water, was added to the above solution, stirred at room temperature for 8 hours and allowed to stand to separate into layers. The upper organic phase was concentrated in vacuo. The concentrate was slurried with 800 mL of ethyl acetate and filtered, repeated for 4 times. The filter cake was added to a reaction flask, into which 550 mL of ethyl acetate and 306 mL of water were added and 210 mL of 4 mmol/L hydrochloric acid was added dropwise, then the mixture was stirred at room temperature for about 4 hours and allowed to stand to separate into layers. The upper organic phase was concentrated in vacuo to give crude 2-(2-(4-fluorobenzoyl)phenylamino)-3-(4-(2-(9H-carbazol-9-yl)ethoxy)phenyl)propanoic acid (41.46 g). The crude product was recrystallized with about 373 mL of acetonitrile for 3 times to give pure 2-(2-(4-fluorobenzoyl)phenylamino)-3-(4-(2-(9H-carbazol-9-yl)ethoxy)phenyl) propanoic acid. The weight was 23.88 g, the yield was 41.7%, the purity (HPLC) was 99.4%, and the LC-MS (m/z) was 573 (M+1). $^1$H NMR (DMSO-$d_6$) δ 2.98 (dd, 1H, CH2), 3.11 (dd, 1H, CH2), 4.28 (t, 1H, CH), 4.48 (m, 2H, CH2), 4.73 (t, 2H, CH2), 6.59 (d, 1H, Ar—H), 6.68 (d, 2H, Ar—H), 6.60 (d, 1H, Ar—H), 7.05 (d, 2H, Ar—H), 7.18 (d, 2H, Ar—H), 7.31 (m, 3H, Ar—H), 7.42 (m, 3H, Ar—H), 7.61 (m, 4H, Ar—H), 8.13 (d, 2H, Ar—H), 8.50 (d, 1H, NH).

Example 2: Preparation of 2-(2-(4-fluorobenzoyl)phenylamino)-3-(4-(2-(9H-carbazol-9-yl)ethoxy)phenyl)propanoic Acid

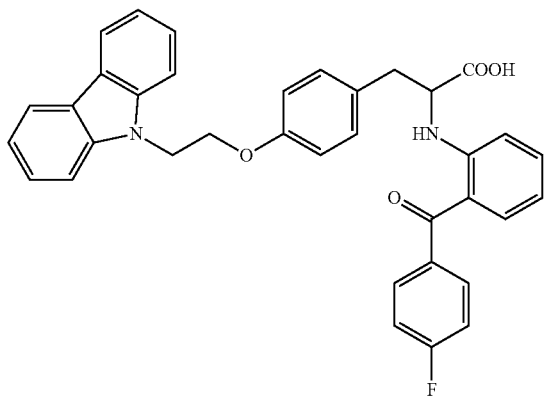 [SMILES: O=C(c1ccc(F)cc1)c1ccccc1NC(Cc1ccc(OCCn2c3ccccc3c3ccccc32)cc1)C(=O)O]

40 mL of toluene, 3.93 g (10 mmol) of methyl 2-[2-(4-fluorobenzoyl)phenyl)amino]-3-(4-hydroxyphenyl)propionate, 4.34 g (15 mmol) of 9-carbazole ethanol mesylate and 3.95 g (12 mmol) of cesium carbonate were sequentially added to a reaction flask, then the mixture was reacted at 80° C. for 2 hours, filtrated, and the filtrate was concentrated in vacuum to remove the solvent toluene to give crude methyl 2-[2-(4-fluorobenzoyl)phenyl)amino]-3-(4-hydroxyphenyl)propionate. The LC-MS (m/z) was 587 (M+1). The crude product obtained was used in the next step without further purification.

The above crude methyl 2-[2-(4-fluorobenzoyl)phenyl)amino]-3-(4-hydroxyphenyl)propionate and 40 mL of tetrahydrofuran were added to the reaction flask and dissolved with stirring at room temperature. 1.68 g (40 mmol) of LiOH.H$_2$O, which had been dissolved in 20 mL of water, was added to the above solution, stirred at 15° C. for 8 hours and allowed to stand to separate into layers. The upper organic phase was concentrated in vacuo. The concentrate was slurried with 70 mL of ethyl acetate and filtered, repeated for 4 times. The filter cake was added to a reaction flask, into which 54 mL of ethyl acetate and 28 mL of water were added and 21 mL of 4 mmol/L hydrochloric acid was added dropwise, the mixture was stirred at room temperature for about 4.5 hours and allowed to stand to separate into layers. The upper organic phase was concentrated in vacuum to give crude 2-(2-(4-fluorobenzoyl)phenylamino)-3-(4-(2-(9H-carbazol-9-yl)ethoxy)phenyl) propanoic acid (4.79 g). The crude product was recrystallized with about 48 mL of acetonitrile for 4 times to give pure 2-(2-(4-fluorobenzoyl)phenylamino)-3-(4-(2-(9H-carbazol-9-yl)ethoxy)phenyl)propanoic acid. The weight was 2.20 g, the yield was 38.5% and the purity (HPLC) was 99.4%.

Example 3: Preparation of 2-(2-(4-fluorobenzoyl)phenylamino)-3-(4-(2-(9H-carbazol-9-yl)ethoxy)phenyl)propanoic Acid

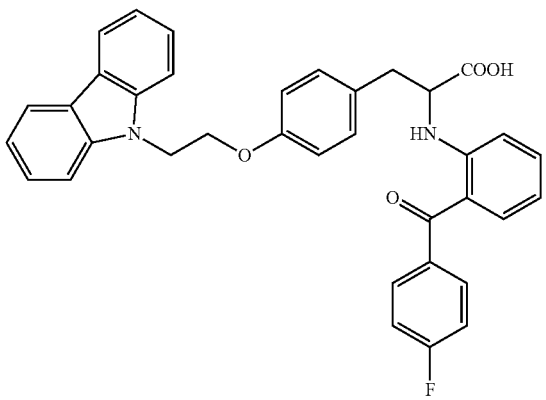 [SMILES: O=C(c1ccc(F)cc1)c1ccccc1NC(Cc1ccc(OCCn2c3ccccc3c3ccccc32)cc1)C(=O)O]

40 mL of toluene, 3.93 g (10 mmol) of methyl 2-[2-(4-fluorobenzoyl)phenyl)amino]-3-(4-hydroxyphenyl)propionate, 4.34 g (15 mmol) of 9-carbazole ethanol mesylate and 3.95 g (12 mmol) of cesium carbonate were sequentially added to a reaction flask, then the mixture was reacted at 120° C. for 2 hours before filtrated, and the filtrate was concentrated in vacuo to remove the solvent toluene to give crude methyl 2-[2-(4-fluorobenzoyl)phenyl)amino]-3-(4-hydroxyphenyl)propionate. The LC-MS (m/z) was 587 (M+1). The crude product obtained was used in the next step without further purification.

The above crude methyl 2-[2-(4-fluorobenzoyl)phenyl)amino]-3-(4-hydroxyphenyl)propionate and 40 mL of tetrahydrofuran were added to the reaction flask and dissolved with stirring at room temperature. 1.68 g (40 mmol) of LiOH.H$_2$O, which had been dissolved in 20 mL of water, was added to the above solution, stirred at 45° C. for 8 hours and allowed to stand to separate into layers. The upper organic phase was concentrated in vacuo. The concentrate was slurried with 80 mL of ethyl acetate and filtered, repeated for 4 times. The filter cake was added to a reaction flask, into which 54 mL of ethyl acetate and 30 mL of water were added and 21 mL of 4 mmol/L hydrochloric acid was added dropwise, before the mixture was stirred at room temperature for about 4.5 hours and allowed to stand to separate into layers. The upper organic phase was concentrated in vacuum to give crude 2-(2-(4-fluorobenzoyl)phenylamino)-3-(4-(2-(9H-carbazol-9-yl)ethoxy)phenyl)propanoic acid (5.25 g). The crude product was recrystallized with about 53 mL of acetonitrile for 4 times to give pure 2-(2-(4-fluorobenzoyl)phenylamino)-3-(4-(2-(9H-carbazol-9-yl)ethoxy)phenyl)propanoic acid. The weight was 2.31 g, the yield was 40.4% and the purity (HPLC) was 99.4%.

Example 4: Preparation of 2-(2-(4-fluorobenzoyl)phenylamino)-3-(4-(2-(9H-carbazol-9-yl)ethoxy)phenyl)propanoic Acid

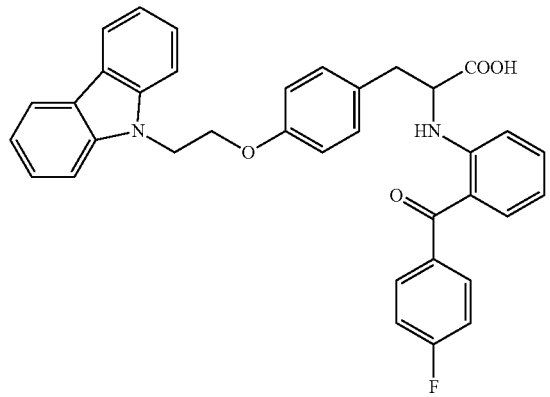 [SMILES: O=C(c1ccc(F)cc1)c1ccccc1NC(Cc1ccc(OCCn2c3ccccc3c3ccccc32)cc1)C(=O)O]

40 mL of toluene, 3.93 g (10 mmol) of methyl 2-[2-(4-fluorobenzoyl)phenyl)amino]-3-(4-hydroxyphenyl)propionate, 4.34 g (15 mmol) of 9-carbazole ethanol mesylate and 3.90 g (12 mmol) of cesium carbonate were sequentially added to a reaction flask, then the mixture was reacted at 90° C. for 2.5 hours before filtration, and the filtrate was concentrated in vacuum to remove the solvent toluene to give crude methyl 2-[2-(4-fluorobenzoyl)phenyl)amino]-3-(4-hydroxyphenyl)propionate. The LC-MS (m/z) was 587 (M+1). The crude product obtained was used in the next step without further purification.

The above crude methyl 2-[2-(4-fluorobenzoyl)phenyl)amino]-3-(4-hydroxyphenyl) propionate and 40 mL of N,N-dimethylformamide were added to the reaction flask and dissolved with stirring at room temperature. 1.67 g (40 mmol) of LiOH.H$_2$O, which had been dissolved in 20 mL of water, was added to the above solution, stirred at room temperature for 4 hours and filtered. The filter cake was slurried with 55 mL of ethyl acetate and filtered, repeated for 4 times. The filter cake was added to a reaction flask, into which 40 mL of ethyl acetate and 22 mL of water were added and 18 mL of 4 mmol/L hydrochloric acid was added dropwise, before the mixture was stirred at room temperature for about 1.5 hours and allowed to stand to separate into layers. The upper organic phase was concentrated in vacuo to give crude 2-(2-(4-fluorobenzoyl)phenylamino)-3-(4-(2-(9H-carbazol-9-yl)ethoxy)phenyl)propanoic acid (3.48 g). The crude product was recrystallized with about 35 mL of acetonitrile twice, to give pure 2-(2-(4-fluorobenzoyl)phenylamino)-3-(4-(2-(9H-carbazol-9-yl)ethoxy)phenyl)propanoic acid. The weight was 2.22 g, the yield was 38.8% and the purity (HPLC) was 99.3%.

The above examples are merely illustrative of the present invention. However, it should be understood that these examples do not limit the invention. Variations of the invention now known or further developed are considered to be within the scope of the invention as described herein and claimed.

The invention claimed is:
1. A method for preparing 2-(2-(4-fluorobenzoyl)phenylamino)-3-(4-(2-(9H-carbazol-9-yl) ethoxy)phenyl)propanoic acid, comprising the following steps:
(a) reacting compound (I) with compound (II), to give compound (III);

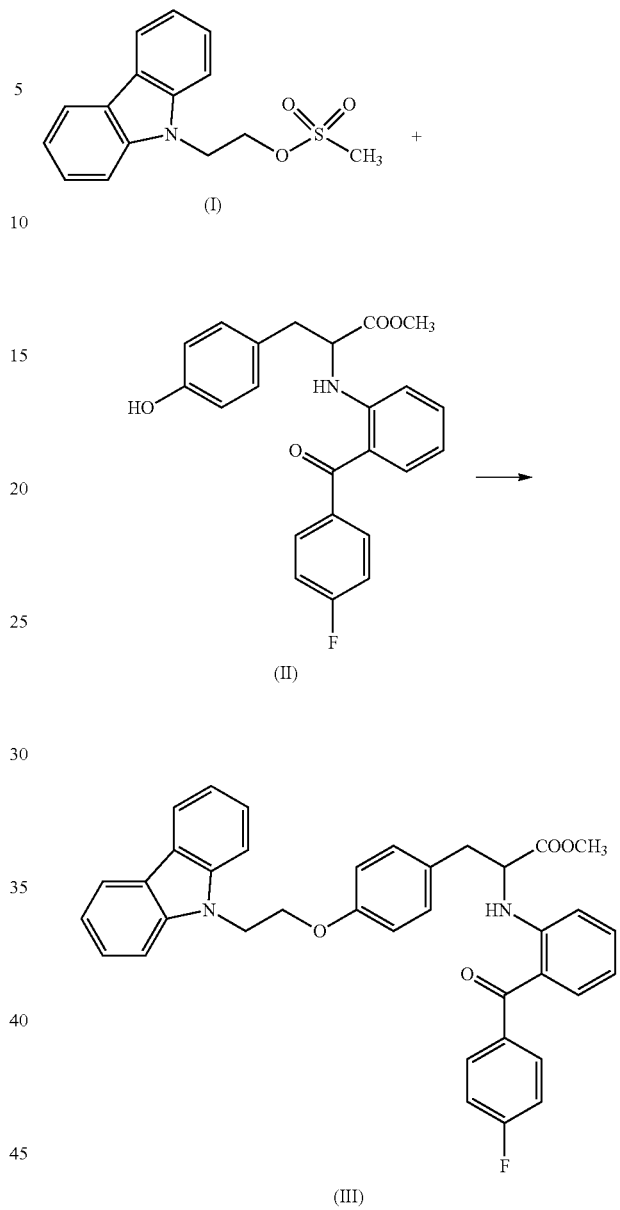

(b) hydrolyzing compound (III) to give compound (IV);

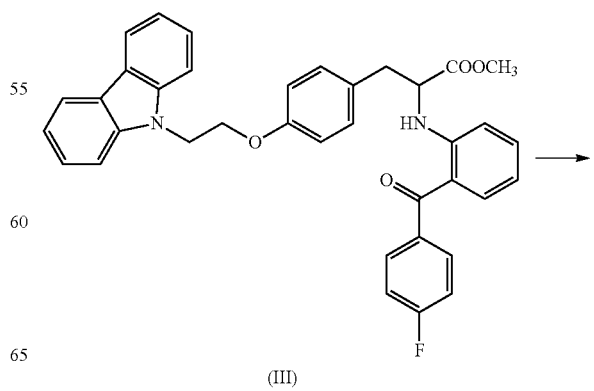

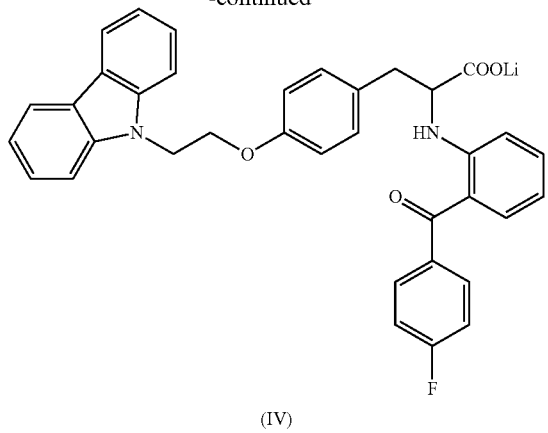

(IV)

(c) acidifying compound (IV) with an acid, to give 2-(2-(4-fluorobenzoyl)phenylamino)-3-(4-(2-(9H-carbazol-9-yl)ethoxy)phenyl)propanoic acid

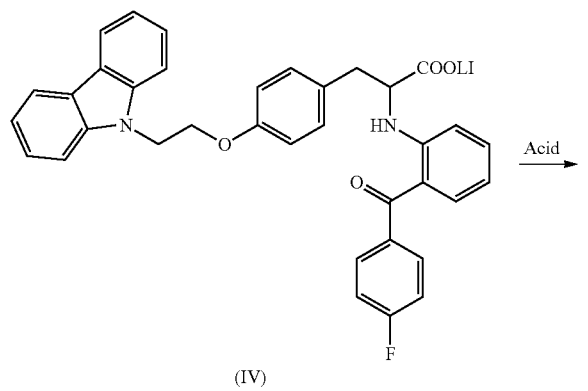

(IV)

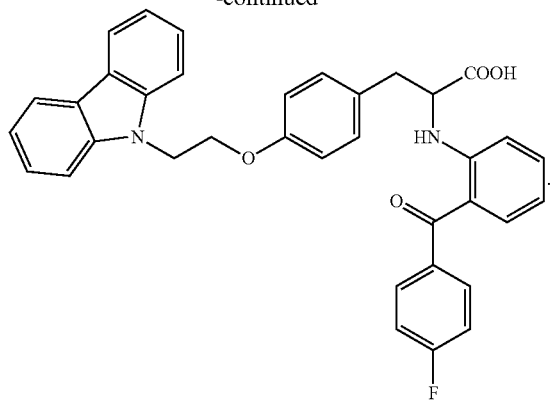

2. The method according to claim 1, wherein step (a) is carried out in the presence of cesium carbonate.

3. The method according to claim 1, wherein step (a) is carried out at a temperature between 80 and 120° C.

4. The method according to claim 1, wherein step (a) is carried out by using toluene as a solvent.

5. The method according to claim 1, wherein the hydrolysis of step (b) is conducted in the presence of a base.

6. The method according to claim 1, wherein the hydrolysis of step (b) is conducted in the presence of lithium hydroxide.

7. The method according to claim 1, wherein the step (b) is carried out by using N, N-dimethylformamide and water or tetrahydrofuran and water as a solvent.

8. The method according to claim 1, wherein step (c) is carried out in the presence of an inorganic acid.

9. The method according to claim 1, wherein step (c) is carried out in the presence of hydrochloric acid.

10. The method according to claim 1, wherein step (c) is carried out by using ethyl acetate and water as a solvent.

\* \* \* \* \*